(12) United States Patent
Tsukamoto et al.

(10) Patent No.: US 11,970,243 B2
(45) Date of Patent: Apr. 30, 2024

(54) BICYCLE EXERCISE MEASUREMENT DEVICE AND BICYCLE

(71) Applicant: HONDA MOTOR CO., LTD., Tokyo (JP)

(72) Inventors: Kenji Tsukamoto, Saitama (JP); Yoshihiro Namiki, Saitama (JP); Satoshi Honda, Saitama (JP); Hiroyuki Kikuchi, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 912 days.

(21) Appl. No.: 16/977,372

(22) PCT Filed: Feb. 5, 2019

(86) PCT No.: PCT/JP2019/004106
§ 371 (c)(1),
(2) Date: Sep. 1, 2020

(87) PCT Pub. No.: WO2019/171858
PCT Pub. Date: Sep. 12, 2019

(65) Prior Publication Data
US 2021/0052941 A1 Feb. 25, 2021

(30) Foreign Application Priority Data
Mar. 5, 2018 (JP) ................. 2018-039070

(51) Int. Cl.
*B62M 6/55* (2010.01)
*A63B 24/00* (2006.01)
(Continued)

(52) U.S. Cl.
CPC .......... *B62M 6/55* (2013.01); *A63B 24/0062* (2013.01); *B62J 43/20* (2020.02); *B62J 45/41* (2020.02);
(Continued)

(58) Field of Classification Search
CPC ....... A61B 5/22; A63B 24/0062; A63B 71/06; A63B 2220/51; A63B 2220/833;
(Continued)

(56) References Cited

U.S. PATENT DOCUMENTS 5,027,303 A 6/1991 Witte
5,772,547 A 6/1998 Terada
(Continued)

FOREIGN PATENT DOCUMENTS

CH 697413 B1 9/2008
CN 200954847 Y 10/2007
(Continued)

OTHER PUBLICATIONS

International Search Report for JP Application PCT/JP2019/004106 dated Mar. 12, 2019; 1 pp.
(Continued)

*Primary Examiner* — Kevin Hurley
*Assistant Examiner* — Felicia L. Brittman
(74) *Attorney, Agent, or Firm* — Armstrong Teasdale LLP

(57) ABSTRACT

An exercise measurement device comprises a housing for attaching to a frame of a bicycle, a generator, an annular rotational input member for rotationally driving the generator, the rotational input member being rotatably mounted on the housing and positioned around a crank axis line, a connecting member connecting the rotational input member to the crankshaft or the crank arm in a torque transmitting relationship, a sensor for detecting at least one of electric current of the generator, a rotational speed of the generator or the crank arm, a torque of the crank arm, a position of the crank arm, a strain in the crank arm, and a pressure on the pedal, a measurement computing unit for computing at least one of power and a pedaling force from an output of the
(Continued)

sensor, and a display unit for displaying a computed value of the measurement computing unit.

5 Claims, 10 Drawing Sheets

(51) Int. Cl.
*B62J 43/20* (2020.01)
*B62J 45/41* (2020.01)
*B62J 45/42* (2020.01)
*B62J 50/22* (2020.01)
*B62M 9/00* (2006.01)

(52) U.S. Cl.
CPC ............... *B62J 45/42* (2020.02); *B62J 50/22* (2020.02); *B62M 9/00* (2013.01); *A63B 2220/51* (2013.01); *A63B 2220/833* (2013.01)

(58) Field of Classification Search
CPC ... B62M 6/50; B62M 6/55; B62M 9/00; B62J 43/20; B62J 45/41; B62J 45/42; B62J 45/411; B62J 45/413; B62J 50/22
USPC ...................................................... 280/288.4
See application file for complete search history.

(56) References Cited

U.S. PATENT DOCUMENTS

| | | |
|---|---|---|
| 2003/0074985 A1 | 4/2003 | Liao |
| 2013/0001000 A1 | 1/2013 | Krieger et al. |
| 2015/0122565 A1 | 5/2015 | Deleval |
| 2016/0023081 A1 | 1/2016 | Popa-Simil et al. |
| 2016/0136481 A1 | 5/2016 | Iverson et al. |

FOREIGN PATENT DOCUMENTS

| | | |
|---|---|---|
| CN | 203172838 U | 9/2013 |
| CN | 204432848 U | 7/2015 |
| CN | 206370721 U | 8/2017 |
| DE | 102012012270 A1 | 12/2012 |
| DE | 102011082082 A1 | 3/2013 |
| DE | 102015107843 A1 | 2/2016 |
| EP | 1298050 A1 | 4/2003 |
| EP | 2332811 A1 | 6/2011 |
| EP | 2477881 A1 | 7/2012 |
| FR | 2983454 A1 | 6/2013 |
| GB | 786655 A | 11/1957 |
| JP | 2000510562 A | 8/2000 |
| JP | 2003282322 A | 10/2003 |
| JP | 2013043528 A | 3/2013 |
| JP | 3137166 U | 11/2017 |
| KR | 20090123824 A | 12/2009 |
| KR | 20120001414 A | 1/2012 |
| KR | 20160019590 A | 2/2016 |
| KR | 20160091478 A | 8/2016 |
| WO | 2017165448 A1 | 9/2017 |

OTHER PUBLICATIONS

EP Office Action for Patent Application EP 19763378.7 dated Oct. 26, 2021; 7 pp.
EPO Extended Search Report for EP Application 19763378.7 dated Feb. 24, 2021; 9 pp.
Notice of Reasons for Refusal for Patent Application JP 2020-504866; 8 pp.

BICYCLE EXERCISE MEASUREMENT DEVICE AND BICYCLE

CROSS-REFERENCE TO RELATED APPLICATIONS

This application is a U.S. National Phase Application of PCT/JP2019/004106, filed Feb. 5, 2019, which claims the benefit of priority to JP Application No. 2018-039070, filed Mar. 5, 2018, the contents of which are hereby expressly incorporated by reference in their entirety.

TECHNICAL FIELD

The present invention relates to a bicycle exercise measurement device and a bicycle, and more particularly to a bicycle exercise measurement device that can be retrofitted and a bicycle to which such an exercise measurement device is installed.

BACKGROUND ART

As an exercise measurement device that measures the amount of exercise such as fitness exercise using an existing bicycle, there is known a device having a rotating member pushed against the rear wheel of the bicycle so as to generate electric power by the rotation of the rotating member, and measuring the amount of exercise from the amount of the generated electric power (see Patent Document 1, for instance).

PRIOR ART DOCUMENT(S)

Patent Document(s)

Patent Document 1: JPU3137166B

SUMMARY OF THE INVENTION

Task to be Accomplished by the Invention

The conventional bicycle exercise measurement device generates electric power for measuring the amount of exercise by transmitting the rotation of the rear wheel tire to the rotating member by frictional force. Therefore, the wearing of the rear wheel tire is caused, and this reduces the service life of the rear wheel tire.

In view of such a problem of the prior art, a primary object of the present invention is to allow the amount of exercise to be measured by using an existing bicycle without reducing the service life of the tire.

To achieve such an object, as an embodiment of the present invention, there is provided a bicycle exercise measurement device, comprising: a housing (52) configured to be attached to a frame (18) of a bicycle (10); a generator (54) attached to the housing (52); an annular rotational input member (81) for rotationally driving the generator (54), the rotational input member being rotatably mounted on the housing and positioned around a crank axis line which is a rotational center line of a crankshaft (24) and a crank arm (26) for a pedal of the bicycle; a connecting member (90, 140) connecting the rotational input member (81) to the crankshaft (24) or the crank arm (26) in a torque transmitting relationship; a sensor (106, 108, 110, 114, 116, 118) for detecting at least one of electric current of the generator (54), a rotational speed of the generator (54) or the crank arm (26), a torque of the crank arm (26), a position of the crank arm (26), a strain in the crank arm, and a pressure on the pedal (130); a measurement computing unit (100) for computing at least one of power and a pedaling force from an output of the sensor; and a display unit (108) for displaying a computed value of the measurement computing unit.

Thereby, the generator (54) serves as a load on a pedaling effort so that the amount of exercise can be measure by using an existing bicycle without impairing the durability of the tire.

In this bicycle exercise measurement device, preferably, the bicycle further includes a battery (102) configured to be mounted to the frame (18) to store electric power generated by the generator (54).

Thereby, the electric power generated by pedaling is effectively utilized while the amount of exercise is measured at the same time.

In this bicycle exercise measurement device, preferably, the housing (52) includes an annular part (52C) that concentrically supports the rotational input member (81), and the rotational input member (81) and the annular part (52C) are positioned between the frame (18) and the crank arm (26).

Thereby, the crank arm (26) can be passed through the rotational input member (81) and the annular part (52C) so that the rotational input member (81) and the annular part (52C) can be positioned between the frame (18) and the crankarm (26) without removing the crankarm (26), and the retrofitting of the bicycle exercise measurement device (50) to the bicycle (10) can be simplified.

In this bicycle exercise measurement device, preferably, the annular part (52C) is provided with a tubular portion (72) defining a central opening (70) through which the crankshaft (72) loosely passes, and the rotational input member (81) is coaxially and rotatably mounted on an outer periphery of the tubular portion (72).

Thereby, the rotational input member (81) can be supported with a simple structure by using the tubular portion (72) that defines the central opening (70).

Preferably, this bicycle exercise measurement device further comprises a transmission gear train (59) received in the housing (52) and configured to transmit a rotational motion of the rotational input member (81) to the generator (54), the generator (54) being displaced radially outward from the rotational input member (81) via the transmission gear train (59) which is positioned between the generator (54) and the rotational input member (81).

Thereby, the generator (54) allows the rotational input member (81) to be mounted to the crankshaft (24) without the generator (54) interfering with the crankshaft (24).

In this bicycle exercise measurement device, preferably, the generator (54) is offset in an axial direction relative to the rotational input member (81), and in contact with the frame (18) so that the generator (54) is held rotationally fast to the frame (18).

Thereby, the generator (54) is prevented from rotating relative to the frame (18) in a both simple and reliable manner.

In this bicycle exercise measurement device, preferably, the connecting member (90) coaxially connects the rotational input member (81) to an axial end of the crankshaft (24).

Thereby, the rotational input member (81) can be connected to the crankshaft (24) without a fear of misalignment so that the rotational force (pedaling force) can be favorably transmitted from the crankshaft (24) or the crank arm (26) to the rotational input member (81).

Thereby, the generator (54) does not obstruct the mounting of the rotational input member (81) to the crankarm (26).

A bicycle according to an embodiment of the present invention is fitted with this bicycle exercise measurement device (50).

Thereby, an existing bicycle can be used as an exercise bicycle without the inconvenience of wearing out the tires.

Effect of the Invention

According to the bicycle exercise measurement device of the present invention, an amount of exercise can be measured by using an existing bicycle without the inconvenience of wearing out the tires.

BRIEF DESCRIPTION OF THE DRAWING(S)

DESCRIPTION OF THE PREFERRED EMBODIMENT(S)

A bicycle exercise measurement device according to an embodiment of the present invention is described in the following with reference to FIGS. 1 to 4.

Figure 1:
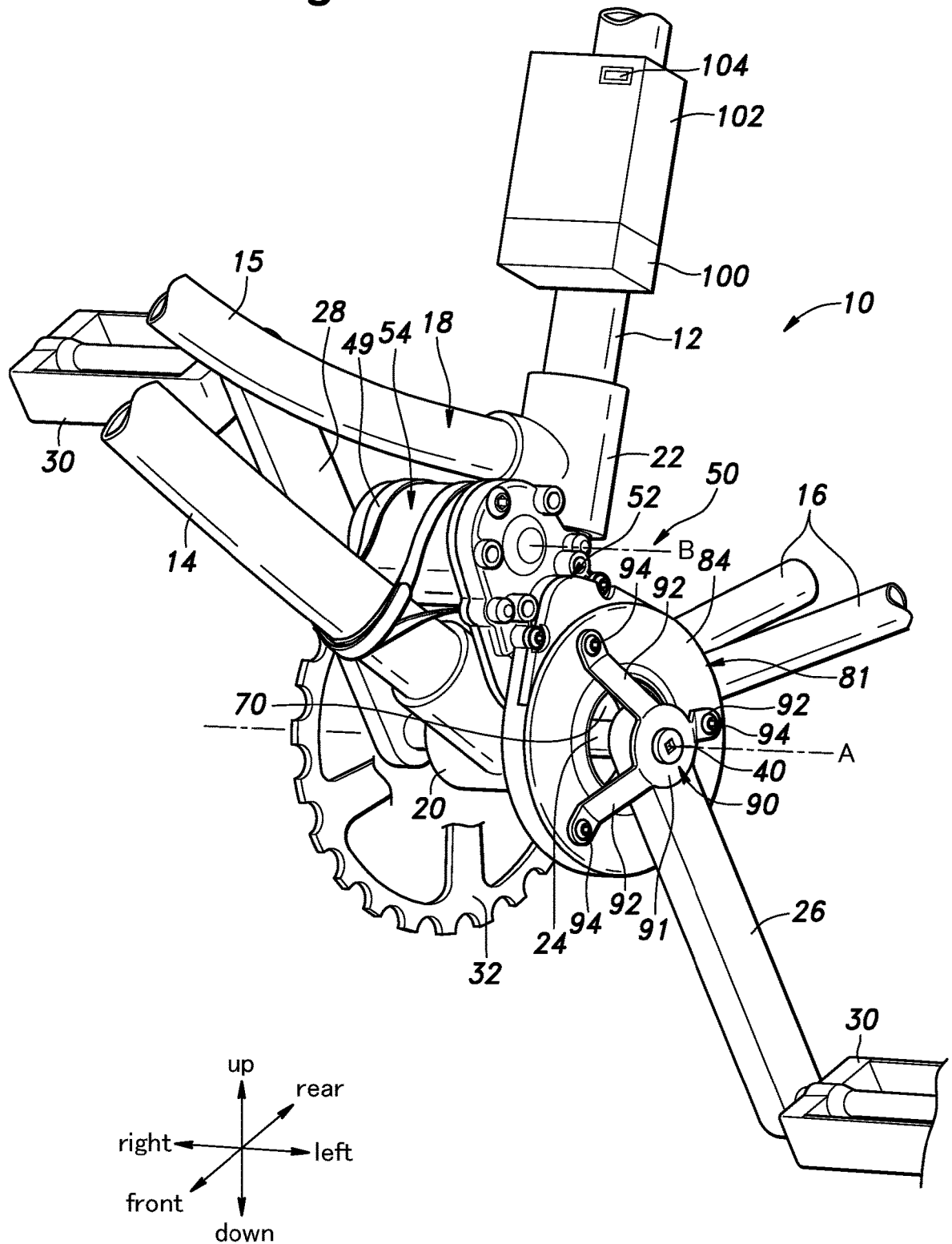
FIG. 1 is a perspective view of a principal part of a bicycle to which a bicycle exercise measurement device according to an embodiment of the present invention is mounted.
Figure 2:
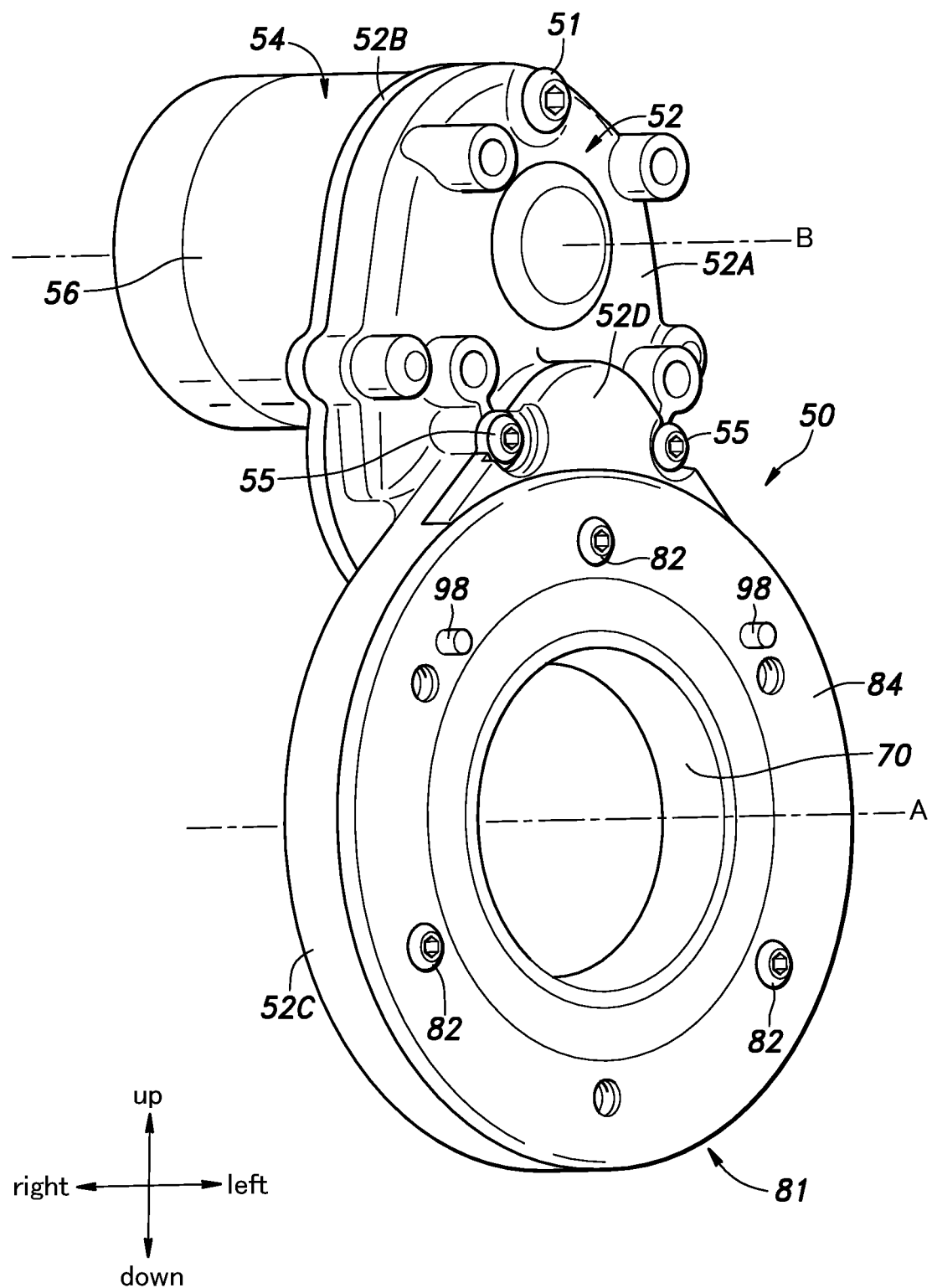
FIG. 2 is a perspective view of the bicycle exercise measurement device according to the embodiment of the present invention.

As shown in FIG. 1, the bicycle 10 is provided with a frame 18 that includes a seat tube 12 that extends substantially in the vertical direction, and is provided with a saddle (not shown in the drawings) attached to the upper end thereof, a down tube 14 and an auxiliary tube 15 that extend in a substantially fore and aft direction, and a pair of chain stays 16. The lower end of the seat tube 12, the rear end of the down tube 14, and the front ends of the chain stays 16 are connected to one another via a tubular bearing housing 20 which serves as a housing for receiving a bearing of a crankshaft as well as a pipe joint. The rear end of the auxiliary tube 15 is connected to a part of the seat tube 12 adjoining the lower end thereof via a pipe joint 22.

The tubular bearing housing 20 rotatably supports a crankshaft (drive shaft) 24 extending substantially horizontally in the lateral direction. The left and right ends of the crankshaft 24 protrude from the tubular bearing housing 20 in the laterally outward direction, and the base ends of a left crank arm 26 and a right crank arm 28 are fixed to the respective shaft ends with a rotational phase difference of 180 degrees. The crankshaft 24 forms the rotational center of the crank arms 26 and 28, and the rotation center axis of the crankshaft 24 and the rotation center axis of the crank arms 26 and 28 coincide with a common crank axis A. In other words, the crank axis A forms the rotation center axis of both the crankshaft 24 and the crank arms 26.

A pedal 30 is attached to the free end of each crank arm 26, 28. A drive sprocket 32 is positioned between the right crank arm 28 and the tubular bearing housing 20. The drive sprocket 32 is coaxially connected (fixed) to the crankshaft 24.

The crankshaft 24 is rotationally driven by the left and right crank arms 26 and 28. When the bicycle 10 is used as a normal means of transportation, the rotation of the crankshaft 24 (rotation in the forward travel direction) is transmitted to the drive sprocket 32, and thence to the rear wheel (not shown in the drawings) via a chain transmission mechanism (not shown in the drawings). Thereby, the bicycle 10 is propelled forward.

So far, this structure is no different from the common existing structure of a bicycle 10.

A bicycle exercise measurement device 50 (which will be abbreviated as "exercise measurement device 50" hereinafter) according to this embodiment is mounted on the tubular bearing housing 20. In the following description, the up, down, front, back, and left and right directions will be based on the viewpoint of a rider when the exercise measurement device 50 is attached to the frame 18 of the bicycle 10 as shown in FIG. 1.

As shown in FIGS. 1 to 4, the exercise measurement device (exercise measuring unit) 50 is provided with a housing 52 having a hollow structure which is formed by an assembly of a first half 52A on the left side, a second half 52B on the right side, and a cover member 52D. The first half 52A and the second half 52B are joined to each other by a plurality of threaded bolts 51. The cover member 52D is joined to the left side of the first half 52A by a plurality of threaded bolts 55.

A motor/generator (rotating electric machine) 54 is attached to the housing 52. The motor/generator 54 is provided with a cylindrical outer casing 56 having a laterally extending central axis B and fixed to the outer surface of the second half 52B at the base end thereof. Thus, the outer casing 56 protrudes rightward from the second half 52B.

The motor/generator 54 is provided with a rotary shaft 58 projecting leftward via the second half 52B into the hollow interior of the housing 52. A small drive spur gear 60 is fixed to the rotary shaft 58. The first half 52A and the second half 52B rotatably support an intermediate shaft 64 extending in the lateral direction via a bush 62 or the like. The intermediate shaft 64 fixedly supports a large-diameter intermediate spur gear 66 that meshes with the drive spur gear 60 on the right side of the bush 62. Thus, the drive spur gear 60 and the intermediate spur gear 66 are accommodated in a first gear chamber 53 defined by the first half 52A and the second half 52B and having a sealed structure. The intermediate shaft 64 is integrally formed with a small-diameter intermediate spur gear 68 formed on the left side of the bush 62.

The first half 52A is integrally formed with an annular part 52C extending downward from a part thereof where the intermediate shaft 64 and the intermediate spur gear 68 are located. The annular part 52C includes a cylindrical portion 72 that defines a central opening 70, a substantially cylindrical outer peripheral portion 74 formed radially outward of and concentrically with the cylindrical portion 72, and a right side portion 76 in the form of an annular plate extending between the cylindrical portion 72 and the outer peripheral portion 74. Thus, the annular part 52C has an open side facing leftward. The central opening 70 has an inner diameter sufficiently larger than the outer diameter of the crankshaft 24, and the crankshaft 24 is passed laterally through the central opening in a loose fit.

An annular large-diameter input spur gear 80 is fitted on the outer periphery of the cylindrical portion 72 via a ball bearing 78 so as to be rotatable around a central axis extending in the lateral direction. Thereby, the input spur gear 80 can be supported with a simple structure by making use of the cylindrical portion 72 defining the central opening 70.

The input spur gear 80 meshes with the intermediate spur gear 68 at the upper side of the input spur gear 80. As a result, a transmission gear train 59 is formed between the drive spur gear 60 and the input spur gear 80 by using mutually parallel shafts fitted with the intermediate spur gear 66 and the intermediate spur gear 68. The transmission gear train 59 transmits the rotation of the input spur gear 80 that forms a part of the rotational input member 81 which will be described later to the motor/generator 54. The transmission gear train 59 using the parallel shafts means a gear mechanism using gears 60, 66, 68, 80 having central axes which are all parallel to one another.

The motor/generator 54 is located at a position spaced radially outward from the rotational input member 81 owing to the arrangement of the transmission gear train 59 using the parallel shafts.

The input spur gear 80 forms a rotational input member 81 jointly with an annular rotational input plate 84 fixed to the left side surface of the input spur gear 80 in a concentric relationship by using a plurality of threaded bolts 82. Thus, the rotational input member 81 includes the input spur gear 80 and the rotational input plate 84, and drives the motor/generator 54 into a rotational motion via the transmission gear train 59.

The entire left side surface of the rotational input plate 84 is exposed to the left on the left side of the annular part 52C, and is rotatable, jointly with input spur gear 80, radially outward of the central opening 70 and around the central axis extending laterally with respect to the cylindrical portion 72. The rotational input member 81 thus rotationally drives the motor/generator 54 via the transmission gear train 59.

The rotational input plate 84 has an outer diameter larger than the outer diameter of the input spur gear 80, and conceals the teeth of the input spur gear 80 and the meshing portion between the input spur gear 80 and the intermediate spur gear 68 from the left side (open side) of the annular part 52C. Thus, the rotational input plate 84 serves as a cover member for the input spur gear 80 to protect the teeth of the input spur gear 80.

The rotational input plate 84 defines a second gear chamber 57 having a sealed structure in cooperation with the annular part 52C and the cover member 52D, and the intermediate spur gear 68 and the input spur gear 80 are accommodated in the second gear chamber 57.

Since the input spur gear 80 and the rotational input plate 84 are both concentric with the central opening 70, and are located radially outward of the cylindrical portion 72, the central opening 70 is exposed to the both sides without being obstructed by the input spur gear 80 or the rotational input plate 84, and extends laterally with a constant inner diameter.

The exercise measurement device 50 can be installed on a bicycle 10 by a worker in the following way.

First of all, the left pedal 30 remote from the drive sprocket 32 is removed by using a common tool such as a spanner. Then, with the exercise measurement device 50 tilted sideways (so that the motor/generator 54 faces upward), the free end of the left crank arm 26 is passed into the central opening 70, and the crank arm 26 is placed in the central opening 70. In this state, the exercise measurement device 50 is moved along the extending direction of the crank arm 26 toward the base end thereof (toward the rotation center side).

Thus, once the crank arm 26 is passed through the rotational input plate 84 and the annular part 52C, the exercise measurement device 50 reaches the vicinity of the base end of the crank arm 26. It should be noted that the inner diameter of the central opening 70 is selected in relation with the outer shape of the crank arm 26 so that this installation process can be executed.

If the central opening 70 has an inner diameter that allows the crank arm 26 with the pedal 30 attached thereto to be passed through the central opening 70, the pedal 30 is not required to be removed from the crank arm 26.

Next, the posture of the exercise measurement device 50 is changed so that the motor/generator 54 is directed in the horizontal direction (the posture shown in FIG. 1) or, in other words, the central axis B of the motor/generator 54 is parallel to the crank axis A. As a result, so that the crankshaft 24 is passed through the central opening 70 in the axial direction in a loose fit. As a result, the rotational input plate 84 and the annular part 52C are positioned between the frame 18 and the crank arm 26 in a loose fit simply by removing the pedal 30 or even without removing the pedal 30.

In this state, the motor/generator 54 is positioned between the auxiliary tube 15 and the down tube 14 which are located one above the other in front of a lower end part of the seat tube 12 as shown in FIG. 1.

Since the motor/generator 54 is located radially outwardly with respect to the rotational input member 81 owing to the positioning of the transmission gear train 59 between the motor/generator 54 and the rotational input member 81, the motor/generator 54 does not interfere with the crankshaft 24, and does not hinder the installation of the rotational input member 81 onto the crankshaft 24.

Since the motor/generator 54 is offset radially outward with respect to the rotational input member 81, the motor/generator 54 includes a part that is located between the auxiliary tube 15 and the down tube 14 which are located one above the other in front of a lower end part of the seat tube 12 as shown in FIG. 1, and overlaps with the frame 18 in plan view and in front view. The motor/generator 54 is prevented from rotating with respect to the frame 18 by the outer casing 56 coming into contact with the down tube 14. As a result, the rotation of the motor/generator 54 with respect to the frame 18 is prevented in a both simple and reliable manner.

The exercise measurement device 50 may be attached to the frame 18 by securing the outer casing 56 of the motor/generator 54 to the down tube 14 by using a fastening band 49 made of rubber, resin, metal, or the like. Here, the housing 52 of the exercise measurement device 50 includes the outer casing 56 of the motor/generator 54. The mounting of the exercise measurement device 50 to the frame 18 by using the fastening band 49 may not be highly secure as long as the exercise measurement device 50 does not rattle against the frame 18 due to vibration or the like. Thus, the securing of the exercise measurement device 50 to the frame 18 is not essential for the present invention, and may even be omitted.

In this mounted state, the rotational input plate 84 is exposed to the left between the tubular bearing housing 20 and the crank arm 26, and is connected to the rotational center of the crank arm 26 or coaxially to the crankshaft 24 via a connecting member 90 attached to this exposed (left) surface so that the rotational force is transmitted from the crank arm 26 to the exercise measurement device 50.

Thereby, this embodiment prevents the durability of the tire of the bicycle 10 from being impaired by wear, and allows the pedaling exercise to be measured by using an existing bicycle 10 in a simple manner.

Since the motor/generator 54 is located radially outward of the annular part 52C and the rotational input plate 84 owing to the presence of the above-mentioned transmission gear train, the motor/generator 54 does not hinder the mounting of the annular part 52C and the input plate 84 to the crank arm 26.

Figure 3:
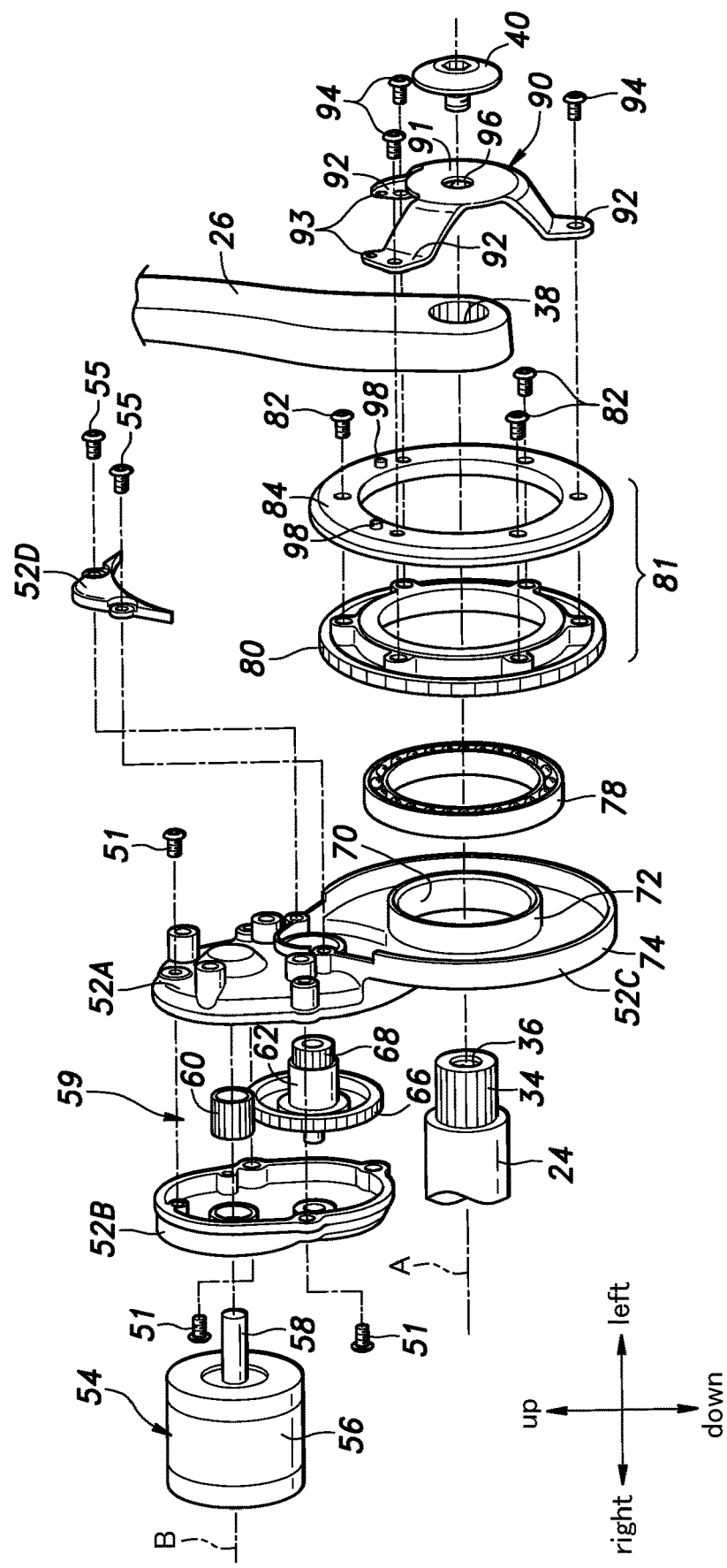
FIG. 3 is an exploded perspective view of the bicycle exercise measurement device and a mounting structure for mounting a generator of the bicycle exercise measurement device to the bicycle according to the embodiment of the present invention.
Figure 4:
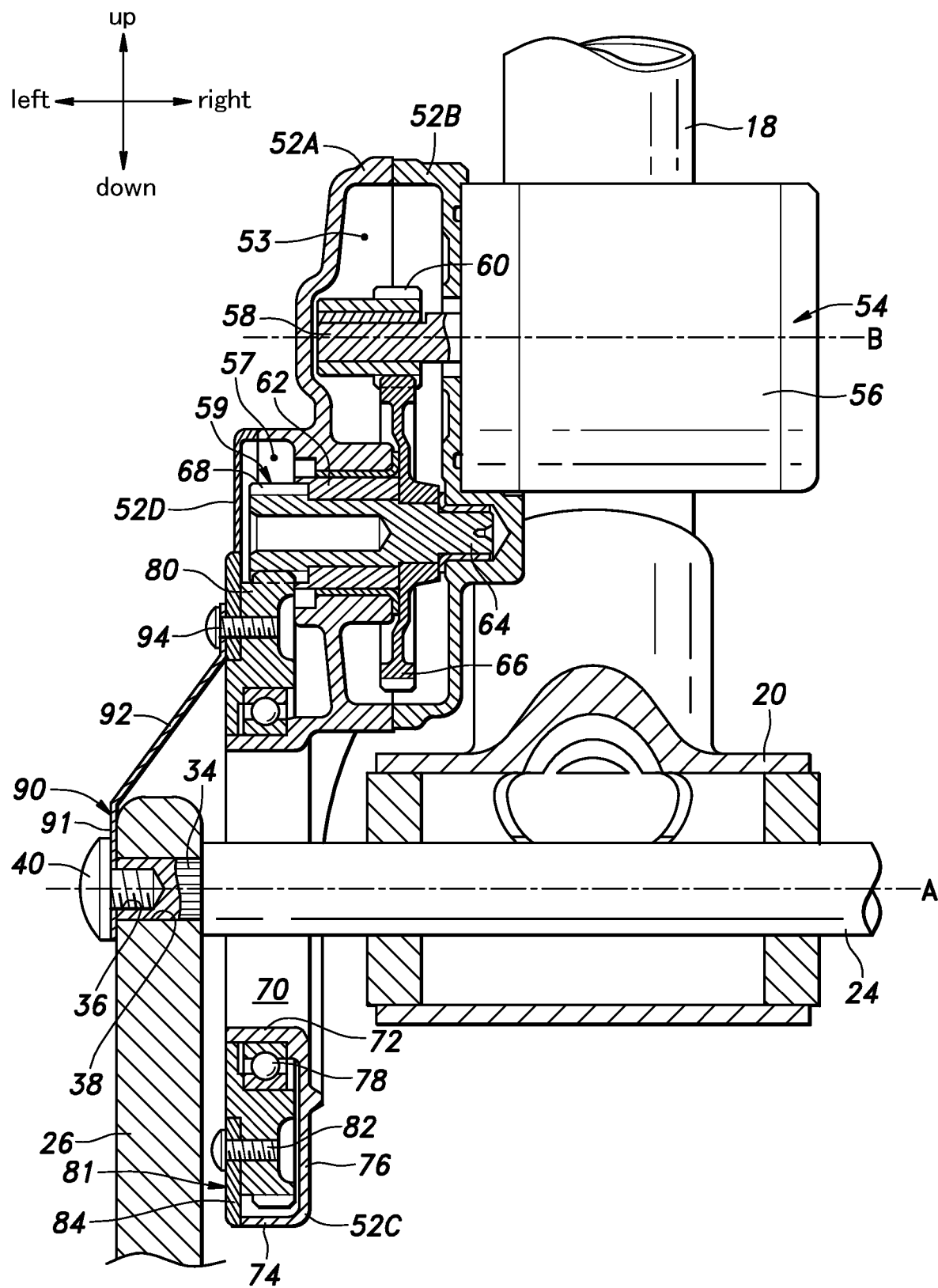
FIG. 4 is a vertical sectional view of the bicycle exercise measurement device according to the embodiment of the present invention.

The connecting structure between the crankshaft 24 and the crank arm 26 in the ordinary bicycle 10 and the connection structure between the rotational input member 81 and the crankshaft 24 via the connecting member 90 are described in the following with reference to FIGS. 3 and 4.

The crankshaft 24 is provided with a splined part 34 having a smaller diameter than the remaining part thereof at an end part thereof. The axial end of the crank arm 26 is centrally provided with a threaded hole 36 for the convenience of removing the crankshaft 24. The base end of the crank arm 26 is provided with a splined hole 38 that is passed laterally through the base end. The splined part 34 is fitted into the splined hole 38 in a spline coupling, and a screw (crank arm fixing screw) 40 is screwed into the threaded hole 36 from the outside of the crank arm 26, whereby the crankshaft 24 and the crank arm 26 are connected to each other so that a rotational force centered around the crank axis A can be transmitted between the crankshaft 24 and the crank arm 26.

The connecting member 90 is provided with a central portion 91 which is secured to the axial end of the crankshaft 24 by the screw 40 which is threaded into the threaded hole 36 of the crankshaft 24, and a plurality of legs 92 each extending radially from the central portion 91 and fixedly secured to the rotational input member 81 by a screw 94 at a free end thereof. Thereby, the rotational input member 81 is connected to the crankshaft 24 in a torque transmitting relationship.

The rotational input plate 84 is provided with a plurality of knock pins 98 which are configured to fit into through holes 93 formed in the free ends of the respective legs 92 (at least two legs) of the connecting member 90 for positioning purpose. Thus, the connecting member 90 is positioned with respect to the rotational input plate 84 so that the connecting member 90 is coaxial with the rotational input plate 84 by fitting the knock pins 98 into the corresponding through holes 93. It should be noted that the inner diameter of the through hole 96 formed in the central portion 91 for the screw 40 may be larger than the outer diameter of the screw 40 so that the central portion 91 may be connected to the crankshaft 24 by the screw 40 after the connecting member 90 is fixedly secured to the rotational input member 81.

As a result, the crankshaft 24 and the rotational input member 81 are concentrically (coaxially) connected to each other by the connecting member 90 and the screw 40 of the existing bicycle 10 in such a manner that the rotation of the crankshaft 24 can be transmitted to the rotational input member 81 without the fear of creating any runout.

According to the exercise measurement device 50 described above, an ordinary user can retrofit the exercise measurement device 50 to any existing bicycle 10 and convert the bicycle 10 into an exercise bicycle with ease without modifying the bicycle and without requiring any special tool or simply by using an ordinary tool such as a spanner, and possibly without even the need to remove the pedal 30.

The exercise measurement is performed with the rear wheel lifted from the floor surface by using a stand or the like so that the rear wheel (not shown in the drawings) can freely rotate. It is also possible to perform the exercise measurement by using the exercise measurement device 50 with the wheels of the bicycle 10 removed. In either case, the durability of the tire of the bicycle 10 is not impaired in any way.

As shown in FIG. 1, a measurement computing/control unit 100 for electric power assist and a battery 102 for storing electric power generated by the motor/generator 54 are secured to the seat tube 12 by using a fastening band (not shown in the drawings) or the like. The battery 102 is provided with a power output unit 104 such as a USB port for power output. The control unit 100 and the battery 102 may be provided separately from the housing 52 and the motor/generator 54 of the exercise measurement device 50, and in such a case, may be electrically connected to the motor/generator 54 by an electric cable (not shown in the drawings).

Thus, a high level of freedom can be achieved in the mode of installing the control 100 and the battery 102 to the bicycle 10, and disassembly and reassembly unit of the bicycle 10 are not required when installing the control unit 100 and the battery 102 to the bicycle 10.

The electrical system of the exercise measurement device 50 is described in the following with reference to FIG. 5.

The measurement computing/control unit 100 is of an electronic control type including a microcomputer or the like, and is configured to compute the pedaling power (power), the pedaling force, the exercise speed (crank rotation speed) and the exercise distance (crank rotation speed× time) are computed, and the charging of the battery 102 by the power generated by the motor/generator 54 is controlled according to various pieces of information such as the information on the current of the motor/generator 54 obtained from the current sensor 106, information on the crank position obtained from the crank position sensor 108, information on the rotational speed of the motor/generator 54 or the crank arm 26 obtained from a rotation sensor 110, and information on the battery voltage of the battery 102 which are forwarded to the measurement computing/control unit 100. As a result, the battery 102 is charged under the control of the measurement computing/control unit 100.

Figure 6:
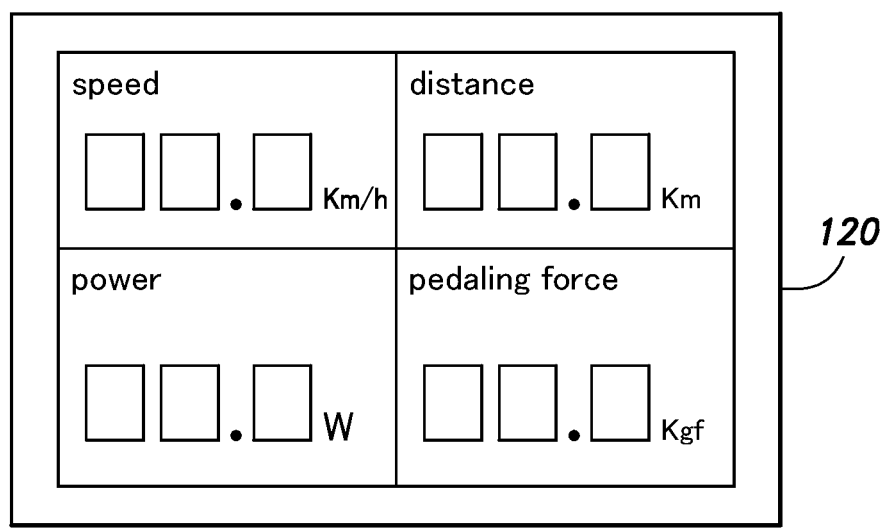
FIG. 6 is a view showing a measured value display on the bicycle exercise measurement device according to the embodiment of the present invention.

A display unit 120 using LCD or the like is connected to the measurement computing/control unit 100. The display unit 120 displays the pedaling power, the pedaling force, the exercise speed, and the exercise distance computed by the measurement computing/control unit 100 on a screen as shown in FIG. 6, for example. The display unit 120 may be a one dedicated to the exercise measurement device 50 or a general-purpose portable terminal such as a smartphone.

The user drives the motor/generator 54 as a pedaling load by rotationally driving the crank arms 26 and 28 by the pedaling of the bicycle 10 to which the exercise measurement device 50 is mounted. Therefore, exercise of a desired level which depends on the power generation load of the motor/generator 54 can be performed. The result of the exercise is displayed on the display unit 120 as discussed above.

Figure 5:
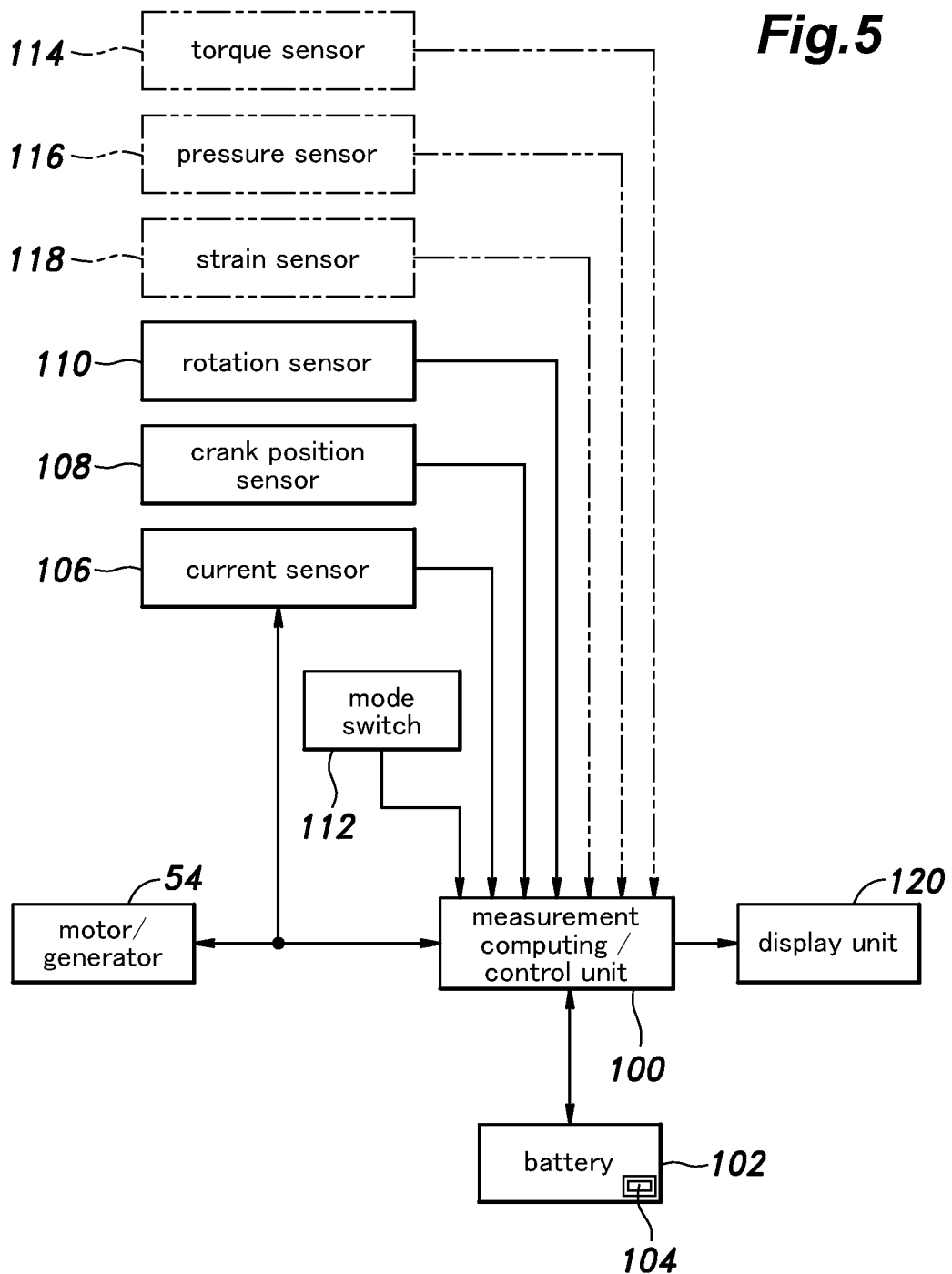
FIG. 5 is a block diagram of an electric system of the bicycle exercise measurement device according to the embodiment of the present invention.
Figure 7:
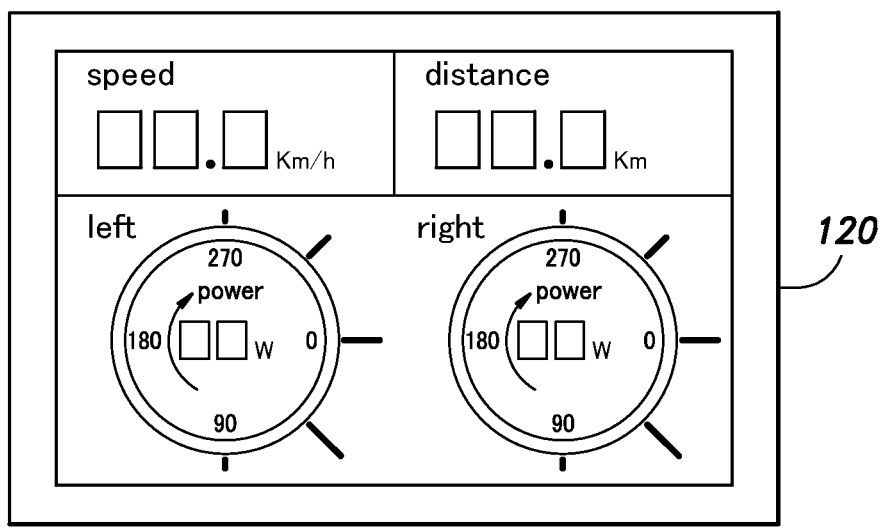
FIG. 7 is a view showing another measured value display on the bicycle exercise measurement device according to the embodiment of the present invention.

As a modified embodiment, the measurement computing/control unit 100 may be configured to compute the pedal pressure on the pedal at prescribed crank positions according to a sensor signal received from at least one of a torque sensor 114 for detecting the torque of the crank arm 26, a pressure sensor for detecting a pressure acting on the pedal 30, and a strain sensor 118 for detecting a strain in the crank arm 26, in addition to the sensor signal from the crank position sensor 108, as shown in FIG. 5. The result of this computing may be shown on the display unit 120 as shown in FIG. 7, for example.

Figure 8A:
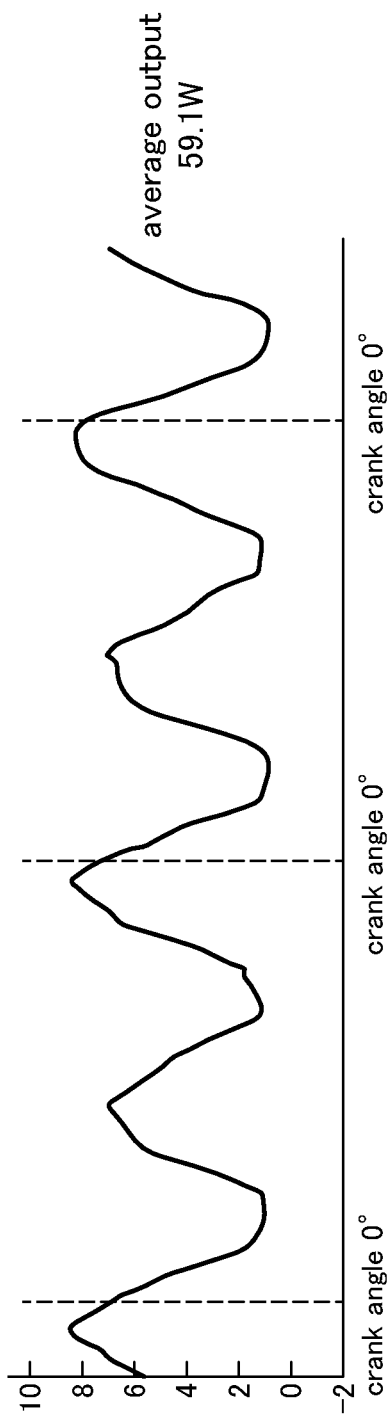
FIG. 8 is a view showing yet another measured value display on the bicycle exercise measurement device according to the embodiment of the present invention.
Figure 8B:
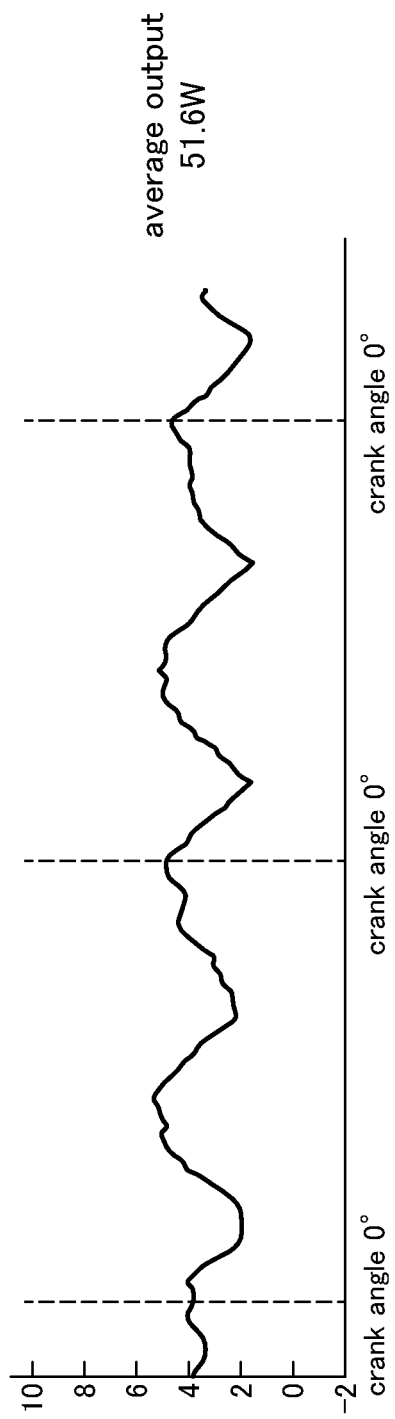

As another modified embodiment, the measurement computing/control unit 100 may be configured to compute the pedaling force at a predetermined crank angle in time series according the current and crank angle of the motor/generator 54, and to display the change in the pedaling force on the screen as a time series graph. The display unit 120 displays the time series graph on the screen as shown in FIG. 8. FIG. 8A shows the time series graph during normal pedaling, and FIG. 8B shows the time series graph during circular pedaling which is considered to be an ideal way of pedaling.

The bicycle 10 fitted with the exercise measurement device 50 generates electric power by the user's exercise, and the electric power charged in the battery 102 by this power generation can be drawn from the power output unit 104. Therefore, the bicycle 10 fitted with the exercise measurement device 50 may be an exercise bike and a pedal-driven electric power generating bicycle at the same time.

In the present embodiment, the motor/generator 54 is rotationally driven by pedaling to measure the amount of exercise and to generate electric power by making use of an existing bicycle 10 in a simple manner without the fear of impairing the durability of the tire of the bicycle 10. In the present embodiment, efficient power generation free from friction loss can be performed.

As shown in FIG. 5, the measurement computing/control unit 100 may be connected to a mode switch 112 so that the user can select between the exercise measurement mode which was described above and an electric assist mode for the bicycle 10.

In the electric assist mode, the motor/generator 54 is used as an electric motor for generating an assist force, and the generated rotational assist force is transmitted from the rotational input plate 84 to the crank arm 26.

Figure 9:
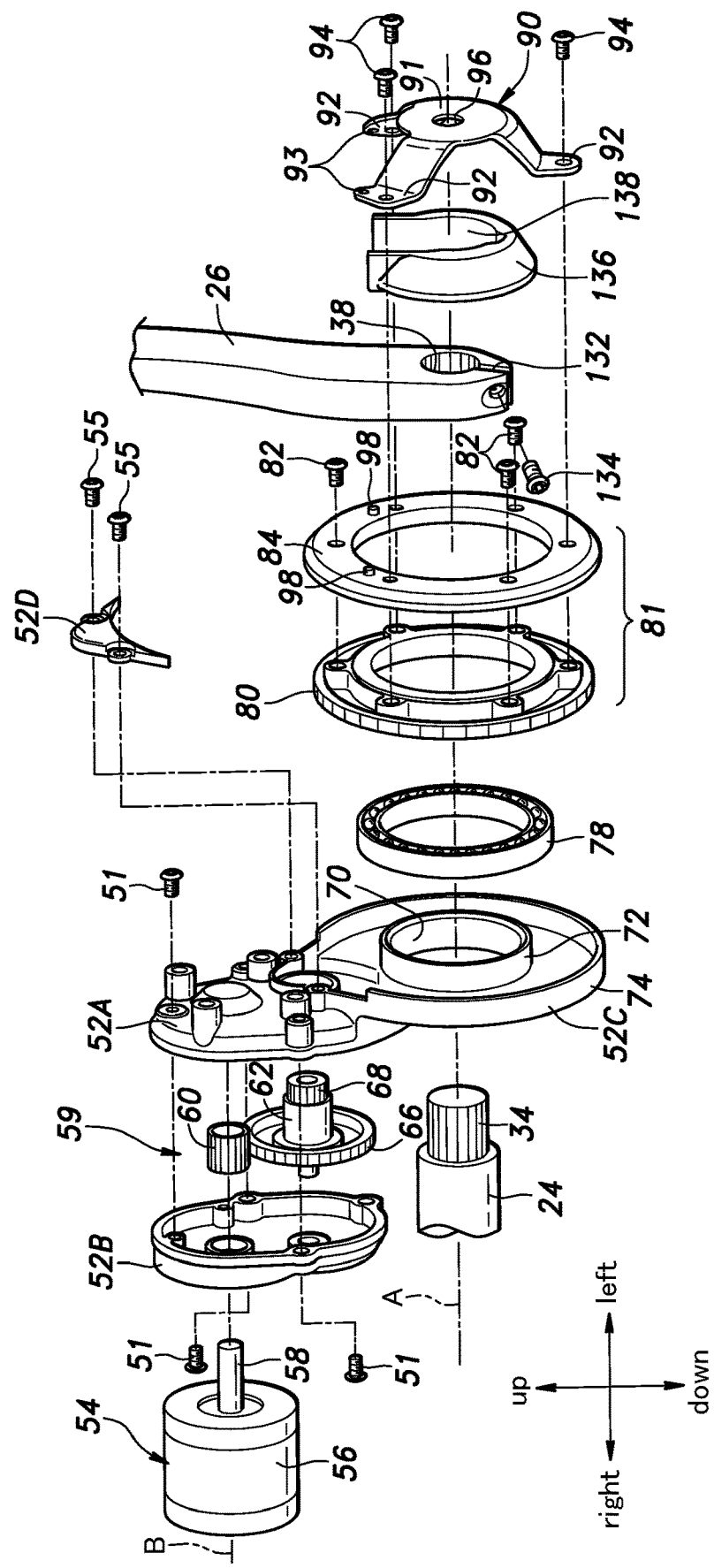
FIG. 9 is an exploded perspective view of a bicycle exercise measurement device and a mounting structure for mounting a generator of the bicycle exercise measurement device to the bicycle according to another embodiment of the present invention.

An exercise measurement device 50 according to another embodiment is described in the following with reference to FIG. 9. This embodiment is applied to a bicycle in which a threaded hole 36 for removing the crankshaft is absent, and the crank arm 26 is connected to the crankshaft 24 by tightening a slit 132 formed in the crank arm 26 with a fastening bolt 134 instead of using a screw 40.

The exercise measurement device 50 including the connecting member 90 used on this bicycle 10 is no different from the one used on the bicycle 10 having the threaded hole 36 for pulling out the crankshaft, and the connecting member 90 is connected to the rotational input member 81 in an identical fashion. In other words, the same connecting member 90 can be used as a common component part for both the bicycle 10 having a threaded hole 36 for pulling out the crankshaft and a bicycle 10 having no such threaded hole.

In the bicycle 10 of this type, a spacer member 136 is used instead of the screw 40. The spacer member 136 surrounds the base end of the crank arm 26 in a U shape (horseshoe shape), and includes a part located between the legs 92 of the connecting member 90 and the outer periphery of the base end of the crank arm 26 so as to surround the base end of the crank arm 26 and define an opening 138 conforming to the base end of the crank arm 26. The spacer member 136 thus connects the connecting member 90 to the crank arm 26 in a torque transmitting relationship.

As a result, the rotational force can be transmitted from the crank arm 26 to the rotational input member 81 via the spacer member 136.

In the bicycle 10 of this type also, an ordinary user can easily retrofit the exercise measurement device 50 to the bicycle 10 without modifying the bicycle 10 or requiring any special tool to convert the bicycle 10 into an exercise bicycle without impairing the durability of the tire in a simple manner.

As described above, the exercise measurement device 50 according to the present embodiment can be mounted to a wide range of existing bicycles, possibly with the optional use of the spacer member 136.

Figure 10:
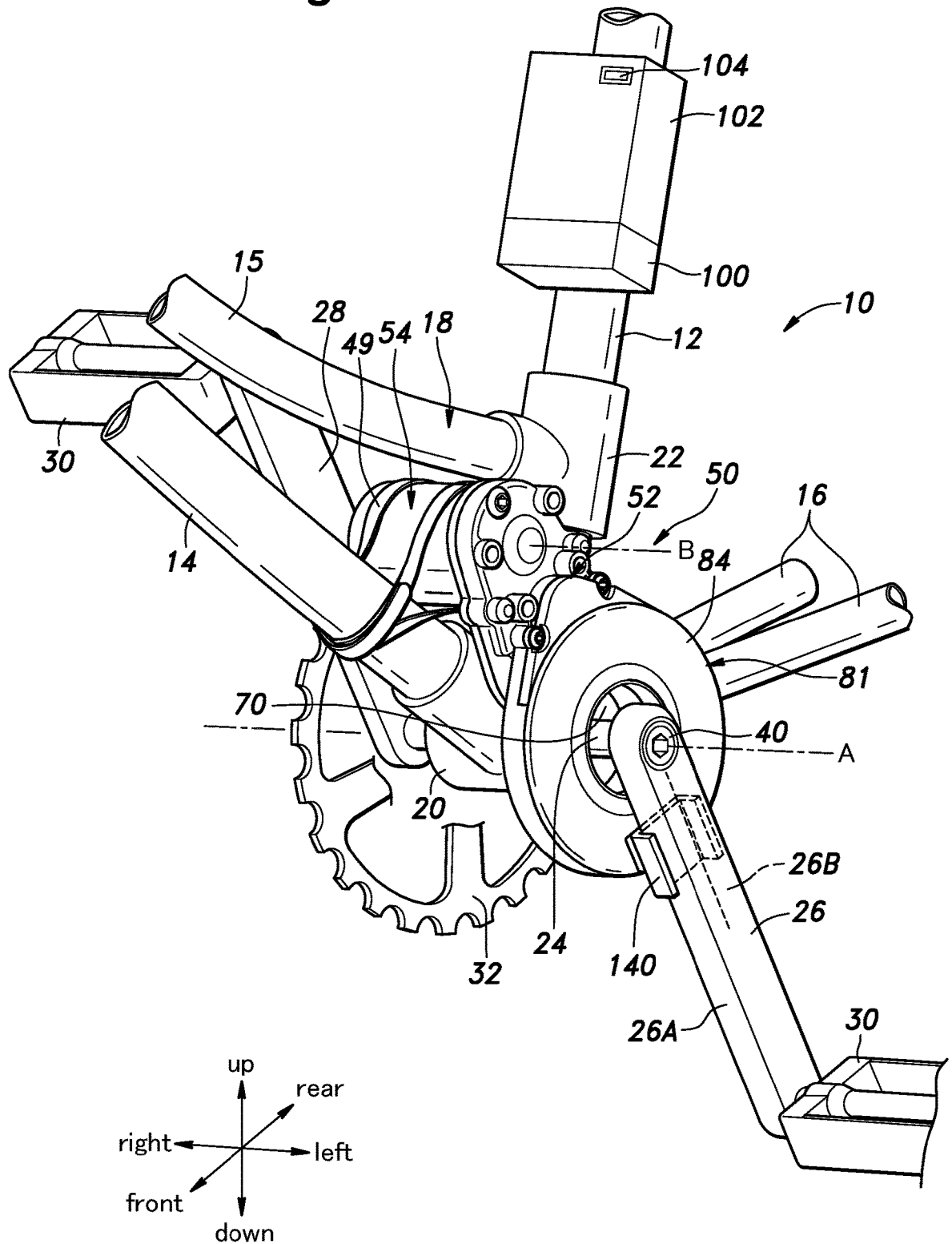
FIG. 10 is a perspective view of the bicycle exercise measurement device according to yet another embodiment of the present invention.

A bicycle exercise measurement device according to yet another embodiment of the present invention is described in the following with reference to FIG. 10. In FIG. 10, the parts corresponding to those in FIG. 1 are denoted with like reference numerals as those in FIG. 1, and description of such parts may be omitted.

In this embodiment, a staple-shaped connecting member 140 is fixed to the rotational input plate 84. The connecting member 140 interposes a base end part of the crank arm 26 from the front and rear so as to be in contact with the front surface 26A and the rear surface 26B of the crank arm 26, and slidable (slidable) along the crank arm 26 in the longitudinal direction of the crank arm 26. In other words, the connecting member 140 is configured to grip the crank arm 26 from both sides with respect to the rotational direction.

According to this embodiment, the connecting member 140 transmits the rotational force from the crank arm 26 to the rotational input plate 84 by sliding relative to the crank arm 26 and accommodating the movement of the crank arm 26 in the longitudinal direction.

In this embodiment also, power generation can be performed by using an existing bicycle without impairing the durability of the tire, and the exercise amount can be measured. In addition, an ordinary user can easily retrofit the exercise measurement device 50 to a wide range of existing bicycles 10 without the need to modify the bicycle 10 and without requiring any special tool so that a wide range of existing bicycles 10 can be converted into exercise bicycles without any difficulty.

The present invention has been described in terms of specific embodiments, but is not limited by such embodiments, and can be modified in various ways without departing from the scope of the present invention. For example, the motor/generator 54 may be prevented from rotating by contacting the auxiliary tube 15, the seat tube 12, or the chain stay 16, instead of the down tube 14. When the exercise measurement device 50 is used solely for exercise measurement, a generator may be used instead of the motor/generator 54. The exercise measurement device 50 may be attached to any other outer part of the bicycle such as the seat tube 12, the down tube 14, the auxiliary tube 15, the chain stay 16, and the pipe joint 22, instead of the tubular bearing housing 20. The gears of the transmission gear train 59 may be helical gears instead of spur gears. In addition, all the components shown in the above embodiment are not necessarily essential to the present invention, and can be appropriately selected, substituted and omitted without departing from the gist of the present invention.

GLOSSARY OF TERMS

| | |
|---|---|
| 10: bicycle | 12: seat tube |
| 14: down tube | 15: auxiliary tube |
| 16: chain stay | 18: frame |
| 20: tubular bearing housing | 22: pipe joint |
| 24: crankshaft | 26: crank arm |
| 26A: front surface | 26B: rear surface |
| 28: crank arm | 30: pedal |
| 32: drive sprocket | 34: splined part |
| 36: screw hole | 38: splined hole |
| 40: screw | 49: fastening band |
| 50: exercise measurement device | 51: bolt |
| 52: housing | 52A: first half |
| 52B: second half | 52C: annular part |
| 52D: cover member | 53: first gear chamber |
| 54: generator | 55: bolt |
| 56: outer casing | 57: second gear chamber |
| 58: rotary shaft | 59: gear train |
| 60: drive spur gear | 62: bush |
| 64: intermediate shaft | 66: intermediate spur gear |
| 68: intermediate spur gear | 70: central opening |
| 72: cylindrical portion | 74: outer peripheral portion |
| 76: right side portion | 78: ball bearing |
| 80: input spur gear | 81: rotational input member |
| 82: bolt | 84: rotation input plate |
| 90: connecting member | 91: central part |
| 92: leg | 93: through hole |
| 94: screw | 96: through hole |
| 98: knock pin | 100: control unit |
| 102: battery | 104: power output unit |
| 106: current sensor | 108: crank position sensor |
| 110: rotation sensor | 112: mode switch |
| 114: torque sensor | 116: pressure sensor |
| 118: sensor | 120: display unit |
| 132: slit | 134: fastening bolt |
| 136: spacer member | 138: opening |
| 140: connecting member | |

The invention claimed is:

1. A bicycle exercise measurement device, comprising:
   a housing configured to be supported by a frame of a bicycle;
   a generator attached to the housing;
   an annular rotational input member for rotationally driving the generator, the rotational input member being rotatably mounted on the housing and positioned around a crank axis line which is a rotational center line of a crankshaft and a crank arm for a pedal of the bicycle;
   a connecting member connecting the rotational input member to the crankshaft or the crank arm in a torque transmitting relationship;
   a sensor for detecting at least one of electric current of the generator, a rotational speed of the generator or the crank arm, a torque of the crank arm, a position of the crank arm, a strain in the crank arm, and a pressure on the pedal;
   a measurement computing unit for computing at least one of power and a pedaling force from an output of the sensor; and
   a display unit for displaying a computed value of the measurement computing unit,
   wherein the housing includes an annular part that concentrically supports the rotational input member, and the rotational input member and the annular part are positioned between the frame and the crank arm, and
   the annular part is provided with a tubular portion defining a central opening through which the crankshaft loosely passes, and the rotational input member is coaxially and rotatably mounted on an outer periphery of the tubular portion, the tubular portion being formed integrally with the annular part of the housing.

2. The bicycle exercise measurement device according to claim 1, wherein the bicycle further includes a battery configured to be mounted to the frame to store electric power generated by the generator.

3. The bicycle exercise measurement device according to claim 1, further comprising a transmission gear train received in the housing and configured to transmit a rotational motion of the rotational input member to the generator, the generator being displaced radially outward from the rotational input member via the transmission gear train which is positioned between the generator and the rotational input member.

4. The bicycle exercise measurement device according to claim 1, wherein the generator is offset in an axial direction relative to the rotational input member, and in contact with the frame so that the generator is held rotationally fast to the frame.

5. A bicycle fitted with the bicycle exercise measurement device according to claim 1.

* * * * *